United States Patent [19]

Ayers et al.

[11] Patent Number: 5,486,198
[45] Date of Patent: Jan. 23, 1996

[54] ATRIAL DEFIBRILLATOR AND METHOD FOR PROVIDING INTERVAL TIMING OF SUCCESSIVE INTERVALS PRIOR TO CARDIOVERSION

[76] Inventors: Gregory M. Ayers, 28308 NE. 146th St., Duvall, Wash. 98052; Clifton A. Alferness, 2202-236th Pl. NE., Redmond, Wash. 98053; Harley G. White, 937-210th Ave. NE., Redmond, Wash. 98053

[21] Appl. No.: 289,701

[22] Filed: Aug. 12, 1994

[51] Int. Cl.⁶ ........................................... A61N 1/39
[52] U.S. Cl. ..................... 607/5; 607/4; 607/14; 128/705
[58] Field of Search ...................... 607/4, 5, 14

[56] References Cited

U.S. PATENT DOCUMENTS

| | | | |
|---|---|---|---|
| 3,738,370 | 6/1973 | Charms | 128/419 D |
| 3,952,750 | 4/1976 | Mirowski et al. | 128/419 D |
| 3,985,142 | 10/1976 | Wickham | 128/419 PG |
| 5,107,850 | 4/1992 | Olive | 128/419 D |
| 5,165,403 | 11/1992 | Mehra | 128/419 D |
| 5,179,945 | 1/1993 | Van Hofwegan et al. | 607/5 |
| 5,282,836 | 2/1994 | Kreyenhagen et al. | 607/4 |
| 5,282,837 | 2/1994 | Adams et al. | 607/4 |
| 5,350,406 | 9/1994 | Mitzsche et al. | 607/14 |
| 5,411,524 | 5/1995 | Rahul | 607/5 |

*Primary Examiner*—William E. Kamm
*Assistant Examiner*—Marianne Parker
*Attorney, Agent, or Firm*—Richard O. Gray, Jr.

[57] ABSTRACT

An atrial defibrillator and method provides cardioverting electrical energy to the atria of a human heart after timing successive R to R intervals. A detector detects ventricular activations of the heart and a timer times intervals between immediately successive ventricular activations. A cardiovertor applies cardioverting electrical energy to the atria of the heart when a second time interval between a third ventricular activation and a second ventricular activation immediately preceding the third ventricular activation satisfies a predetermined criteria with respect to a first time interval between the second ventricular activation and a first ventricular activation immediately preceding the second ventricular activation.

17 Claims, 3 Drawing Sheets

ATRIAL DEFIBRILLATOR AND METHOD FOR PROVIDING INTERVAL TIMING OF SUCCESSIVE INTERVALS PRIOR TO CARDIOVERSION

BACKGROUND OF THE INVENTION

The present invention generally relates to an atrial defibrillator for applying cardioverting electrical energy to the atria of a human heart in need of cardioversion. The present invention is more particularly directed to a fully automatic implantable atrial defibrillator which exhibits improved safety by reducing the potential risk of induced ventricular fibrillation or tachycardia which may result from the mistimed delivery of cardioverting electrical energy to the atria of the heart. More specifically, the atrial defibrillator of the present invention guards against applying cardioverting electrical energy to the atria of the heart under conditions believed to contribute to induced ventricular fibrillation or tachycardia.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well know in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Two such proposed defibrillators, although represented as being implantable, were not fully automatic, requiring human interaction for cardioverting or defibrillating the heart. Both of these proposed defibrillators require the patient to recognize the symptoms of atrial fibrillation, with one defibrillator requiring a visit to a physician to activate the defibrillator, and the other defibrillator requiring the patient to activate the defibrillator with an external magnet.

An improved atrial defibrillator and lead system which exhibits both automatic operation and improved safety is fully described in U.S. Pat. No. 5,282,837, which issued on Feb. 1, 1994, for ATRIAL DEFIBRILLATOR AND METHOD, and which patent is assigned to the assignee of the present invention and is incorporated herein by reference. As disclosed in the aforementioned referenced patent, synchronizing the delivery of the defibrillating or cardioverting electrical energy to the atria with a ventricular electrical activation (R wave) of the heart is important to prevent induced ventricular fibrillation. Ventricular fibrillation is a fatal arrhythmia which can be caused by electrical energy being delivered to the heart at the wrong time in the cardiac cycle, such as during the T wave of the cycle.

The atrial defibrillator of the aforementioned referenced patent exhibits further improved safety from inducing ventricular fibrillation by generating reliable synchronization signals. This is accomplished by sensing ventricular activations of the heart in a manner which rejects noise as ventricular electrical activations. By providing such noise immunity in R wave detection, reliable synchronization is achieved.

Another measure for reducing the risk of inducing ventricular fibrillation during the delivery of cardioverting electrical energy to the atria of the heart employed by the defibrillator of the aforementioned referenced patent is the reduction of the amount of electrical energy which is passed through the ventricles during cardioversion of the atria. This is achieved by locating the cardioverting electrodes to provide a cardioverting energy path which confines most of the cardioverting electrical energy to the atria of the heart.

Another atrial defibrillator and method which provides a still further improvement to the end of safety and reduction in the risk of inducing ventricular fibrillation during atrial cardioversion or defibrillation is described in U.S. Pat. No. 5,207,219, which issued on May 4, 1993, for ATRIAL DEFIBRILLATOR AND METHOD FOR PROVIDING INTERVAL TIMING PRIOR TO CARDIOVERSION, and which patent is also assigned to the assignee of the present invention and is incorporated herein by reference. As described in that patent, it has been observed that during episodes of atrial fibrillation, the cardiac rate may increase to a high rate. At high cardiac rates, the R wave of each cardiac cycle becomes closely spaced from the T wave of the immediately preceding cardiac cycle. This may lead to a condition known in the art as an "R on T" condition which is believed to contribute to induced ventricular fibrillation if the atria are cardioverted in synchronism with an R wave close to a T wave.

The atrial defibrillator and method described in U.S. Pat. No. 5,207,219 greatly reduces this risk by avoiding applying the cardioverting electrical energy to the atria at those instances when increased vulnerability to ventricular fibrillation may be present. This is accomplished by interval timing prior to applying the cardioverting or defibrillating electrical energy. The time interval between immediately successive R waves is timed and the cardioverting or defibrillating electrical energy is applied when a timed interval is greater than a preselected minimum interval. This provides protection for the increased vulnerability to ventricular fibrillation condition resulting from a high cardiac rate.

It is further observed in U.S. Pat. No. 5,207,219 that during highly variable cardiac rates, a long cardiac cycle can be followed by a relatively short cardiac cycle and that this condition in conjunction with a high cardiac rate may cause a dispersion of refractoriness and also may result in an increased vulnerability to ventricular fibrillation or tachycardia. To provide protection for a highly variable cardiac rate, U.S. Pat. No. 5,207,219 suggests a further condition be applied to the timed interval, requiring the timed interval to also be less than a preselected maximum interval before the cardioverting or defibrillating energy is applied to the atria.

While the minimum interval criteria has proven essential in providing safe cardioversion of the atria, there remains room for further improvement. For example, it has been found that a minimum interval sufficiently long so as to be safe under all conditions, including the length of a previous interval and especially where a highly variable cardiac rate is present, limits the number of cardiac cycles which would satisfy the minimum interval criteria. This correspondingly limits the probability of locating an R wave with which to synchronize the cardioverting energy delivery.

The present invention realizes an improvement by increasing the number of such available cycles for synchronizing the energy delivery, while still maintaining safety. This improvement is accomplished in practicing the present invention by requiring a predefined relationship or criteria to be satisfied between a current cardiac interval (one to be used for synchronization) and the interval immediately preceding the current interval. If that criteria is satisfied, the energy may still be delivered safely even though the current interval is less than a minimum interval considered safe under all conditions.

SUMMARY OF THE INVENTION

The invention therefore provides a cardiovertor for providing cardioverting electrical energy to a human heart. The cardiovertor includes detecting means for detecting activations of the heart and interval determining means for determining time intervals between immediately successive activations. The cardiovertor further includes cardioverting means for applying the cardioverting electrical energy to the heart when a second time interval between a third activation and a second activation immediately preceding the third activation satisfies a predetermined criteria with respect to a first time interval between the second activation and a first activation immediately preceding the second activation.

The invention further provides an atrial defibrillator for providing cardioverting electrical energy to the atria of a human heart. The atrial defibrillator includes detecting means for detecting ventricular activations of the heart and interval determining means for determining time intervals between immediately successive ventricular activations. The atrial defibrillator further includes cardioverting means for applying the cardioverting electrical energy to the atria of the heart when a second time interval between a third ventricular activation and a second ventricular activation immediately preceding the third ventricular activation satisfies a predetermined criteria with respect to a first time interval between the second ventricular activation and a first ventricular activation immediately preceding said second ventricular activation.

The present invention still further provides a method for providing cardioverting electrical energy to a human heart. The method includes the steps of detecting activations of the heart, determining time intervals between immediately successive activations, and applying the cardioverting electrical energy to the heart when a second time interval between a third activation and a second activation immediately preceding the third activation satisfies a predetermined criteria with respect to a first time interval between the second activation and an activation immediately preceding said second activation.

The present invention still further provides a method of providing cardioverting electrical energy to the atria of a human heart. The method includes the steps of detecting ventricular activations of the heart, determining time intervals between immediately successive ventricular activations, and applying the cardioverting electrical energy to the atria of the heart when a second time interval between a third ventricular activation and a second ventricular activation immediately preceding the third ventricular activation satisfies a predetermined criteria with respect to a first time interval between the second ventricular activation and a first ventricular activation immediately preceding said second ventricular activation.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
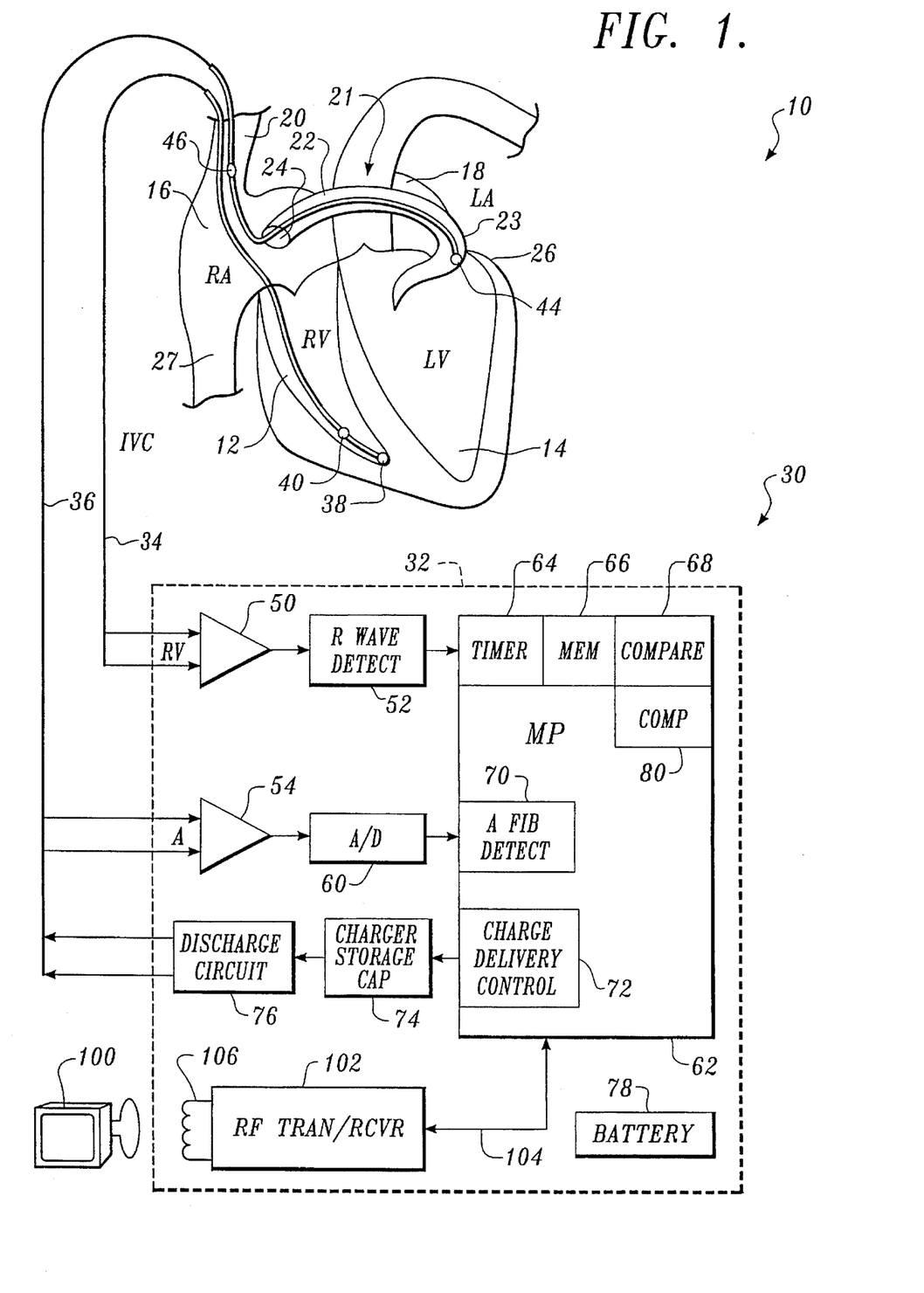
FIG. 1 is a schematic block diagram of a fully implantable atrial defibrillator embodying the present invention for applying cardioverting electrical energy to the atria of the heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "ventricular activations" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is preferably fed through the superior vena cava 20, into the right atrium 16, and then into the right ventricle 12 as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21, either within the coronary sinus 22 adjacent the left ventricle 14 and beneath the left atrium 18, or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10.

Within the enclosure 32, the atrial defibrillator 30 includes a first sense amplifier 50, an R wave detector 52, and a second sense amplifier 54. The first sense amplifier 50 and the R wave detector 52 form a first detecting means which, together with the first lead 34 to which sense amplifier 50 is coupled, senses ventricular activations of the right ventricle 12. The second sense amplifier 54 forms a second detecting means which, together with the first electrode 44 and second electrode 46 of the second lead 36 to which it is coupled, detects atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart. The output of the second sense amplifier 54 is coupled to an analog to digital converter 60 which converts the analog signal representative of the atrial activity of the heart being detected to digital samples for further processing in a manner to be described hereinafter.

The enclosure 32 of the atrial defibrillator 30 further includes a microprocessor 62. The microprocessor 62 is preferably implemented in a manner as will be described hereinafter with respect to the flow diagram of FIG. 2 or, alternatively, as will be described with respect to the flow diagram of FIG. 3. The implementation of the microprocessor 62 in accordance with this embodiment of the present invention results in a plurality of functional stages. The stages include a timer 64, an internal memory 66, a comparator stage 68, an atrial arrhythmia detector in the form of an atrial fibrillation detector 70, a charge delivery and energy control stage 72, and a computation stage 80.

The microprocessor 62 is arranged to operate in conjunction with an external memory (not shown) which may be coupled to the microprocessor 62 by a multiple-bit address bus (not shown) and a bi-directional multiple-bit data bus (not shown). This permits the microprocessor 62 to address desired memory locations within the memory for executing write or read operations. During a write operation, the microprocessor stores data, such as time intervals, or operating parameters in the memory at the addresses defined by multiple-bit addresses conveyed over the address bus and conveys the data to the memory 92 over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters such as minimum intervals or the like into the microprocessor 62, the microprocessor 62 receives the programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in internal memory or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32.

To complete the identification of the various structural elements within the enclosure 32, the atrial defibrillator 30 further includes a charger and storage capacitor circuit 74 of the type well known in the art which charges a storage capacitor to a predetermined voltage level and a discharge circuit 76 for discharging the storage capacitor within circuit 74 for a predetermined discharge time to provide a controlled discharge output of electrical energy when required to the atria of the heart. To that end, the discharge circuit 76 is coupled to the first electrode 44 and the second electrode 46 of the second lead 36 for applying the cardioverting or defibrillating electrical energy to the atria. Lastly, the defibrillator 30 includes a depletable power source 78, such as a lithium battery, for providing power to the electrical components of the atrial defibrillator 30.

If the atrial fibrillation detector 70 determines from the digital samples provided by the analog to digital convertor 60 that the atria 16 and 18 are in fibrillation and thus in need of cardioversion, the charge delivery control 72 causes the charger and storage capacitor circuit 74 to charge the storage capacitor within circuit 74. The atrial defibrillator 30 is now ready to apply the cardioverting electrical energy to the atria in timed relation to an R wave ($R_n$) in a manner as illustrated in the flow diagram of FIG. 2.

Figure 2:
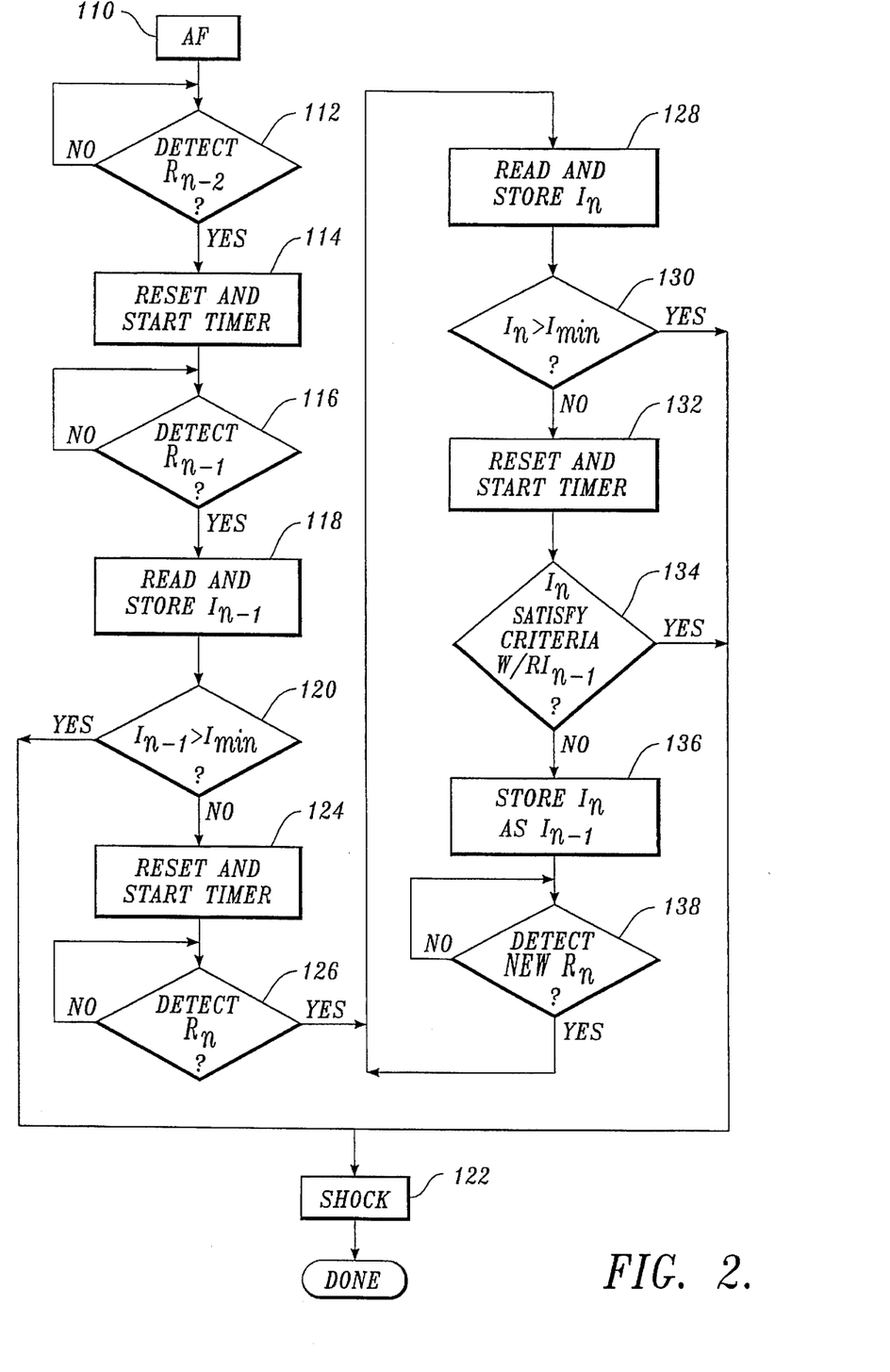
FIG. 2 is a flow diagram illustrating the manner in which the atrial defibrillator of FIG. 1 may be implemented in accordance with a first embodiment of the present invention.

For purposes of describing the implementation of FIG. 2, the R wave ($R_n$) will be referred to herein as the third R wave or ventricular activation, the R wave ($R_{n-1}$) immediately preceding R wave $R_n$ will be referred to herein as the second R wave or ventricular activation, and the R wave ($R_{n-2}$) immediately preceding R wave $R_{n-1}$ will be referred to herein as the first R wave or ventricular activation. Further, the time interval between R wave $R_{n-2}$ and R wave $R_{-1}$ will be referred to herein as the first time interval ($I_{n-1}$), and the time interval between R wave $R_{n-1}$ and R wave $R_n$ will be referred to herein as the second time interval ($I_n$).

After the atrial defibrillator 30 determines that the atria are in fibrillation and the capacitor of circuit 74 is charged as indicated by step 110, the microprocessor 62 in step 112 proceeds to determine if the first R wave ($R_{n-2}$) is being detected. When the sense amplifier 50 and R wave detector 52 detect the first R wave, the microprocessor resets and starts timer 64 in step 114. Following step 114, the microprocessor then determines if the second R wave ($R_{n-1}$) is being detected in step 116. When the second R wave is detected, the microprocessor in step 118 reads the first time interval ($I_{n-1}$) from timer 64 and stores the first time interval in either the internal memory 66 or the aforementioned external memory.

The microprocessor now has the first time interval ($I_{n-1}$) stored in memory. It then in step 120 causes the compare stage 68 to determine if the first time interval is longer than a preselected minimum time interval ($I_{min}$). The preselected minimum time interval is preferably prestored in memory, such as memory 66, after having been obtained from the external programmer 100 as previously described. The preselected minimum time period is also of sufficient duration so as to assure safe cardioversion under all conditions (regardless of the length of the previous interval) including the condition of a variable cardiac rate. To satisfy this criteria, the preselected minimum time interval may, for example, be eight hundred milliseconds (800 ms).

If the first time interval ($I_{n-1}$) is longer than the preselected minimum time interval as determined in step 120, the charge delivery control 72 then in step 122 causes the discharge circuit 76 to discharge the capacitor of circuit 74 for a fixed period of time to apply the cardioverting electrical energy to electrodes 44 and 46 and thus the atria in timed relation to the second R wave ($R_{n-1}$).

If the first time interval ($I_{n-1}$) is not longer than the preselected minimum time interval, the microprocessor then proceeds to step 124 to reset and start timer 64. Following step 124, the microprocessor then, in step 126, determines if the third R wave ($R_n$) is being detected. When the third R wave is detected, the microprocessor then in step 128 reads the second time interval ($I_n$) from the timer 64 and stores the second time interval in either internal memory 66 or the aforementioned external memory.

The microprocessor now has the first time interval ($I_{n-1}$) and the second time interval ($I_n$) stored in memory. It then, in step 130, causes the compare stage 68 to determine if the second time interval is longer than the preselected minimum time interval ($I_{min}$). If the second time interval is longer than the preselected minimum time interval, the charge delivery control 72 in accordance with step 122 causes the discharge circuit 76 to discharge the capacitor of circuit 74 to apply the cardioverting electrical energy to the atria in timed relation to the third R wave ($R_n$).

If the second time interval ($I_n$) is not longer than the preselected minimum time interval, the microprocessor first, in step 132, resets and starts timer 64 and then proceeds to step 134 to determine if the second time interval ($I_n$) satisfies a predetermined criteria with respect to the first time interval ($I_{n-1}$). The predetermined criteria is arranged to assure that the first time interval is not excessively long as compared to the second time interval ($I_n$). If the first time interval is not excessively longer than the second time interval, it will still be safe to apply the cardioverting electrical energy synchronized to or in timed relation to the third R wave ($R_n$), even though the second time interval may be shorter than the preselected minimum time interval. In this manner, the probability of locating an R wave for synchronized energy delivery is increased, while still safely applying the energy to the atria.

The predetermined criteria may, for example, require the second time interval to be longer than the first time interval. To implement this criteria, the compare stage 68 compares the second time interval to the first time interval. This will assure that energy delivery does not occur following a long interval-short interval sequence. An additional requirement is also preferably imposed to satisfy the predetermined criteria. This further requirement is to require the second time interval to be longer than a preselected fail safe minimum time interval to assure that energy delivery does not occur during a high cardiac rate. The preselected fail safe minimum time interval may, for example, be four hundred milliseconds (400 ms).

If the second time interval ($I_n$) satisfies the criteria of step 134, then charge delivery control 72 will cause the discharge circuit to discharge the capacitor of circuit 74, as previously described, to apply the cardioverting energy to the atria synchronized to or in timed relation to the third R wave ($R_n$).

In the event that the second time interval does not satisfy the criteria of step 132 with respect to the first time interval or with respect to the preselected fail safe minimum time interval, the charge delivery control 72 will not cause the cardioverting energy to be applied in timed relation to the third R wave ($R_n$). Instead, the microprocessor will store the second time interval as the first time interval in step 136 and then will proceed to step 138 to determine if the next R wave is being detected. When the next R wave is being detected, the microprocessor then will proceed to step 128 to read and store a new second time interval. The sequence of steps beginning with step 130 will then be repeated as described previously until a suitable interval and hence a suitable R wave is located upon which energy delivery may be timed for safely cardioverting the atria.

Figure 3:
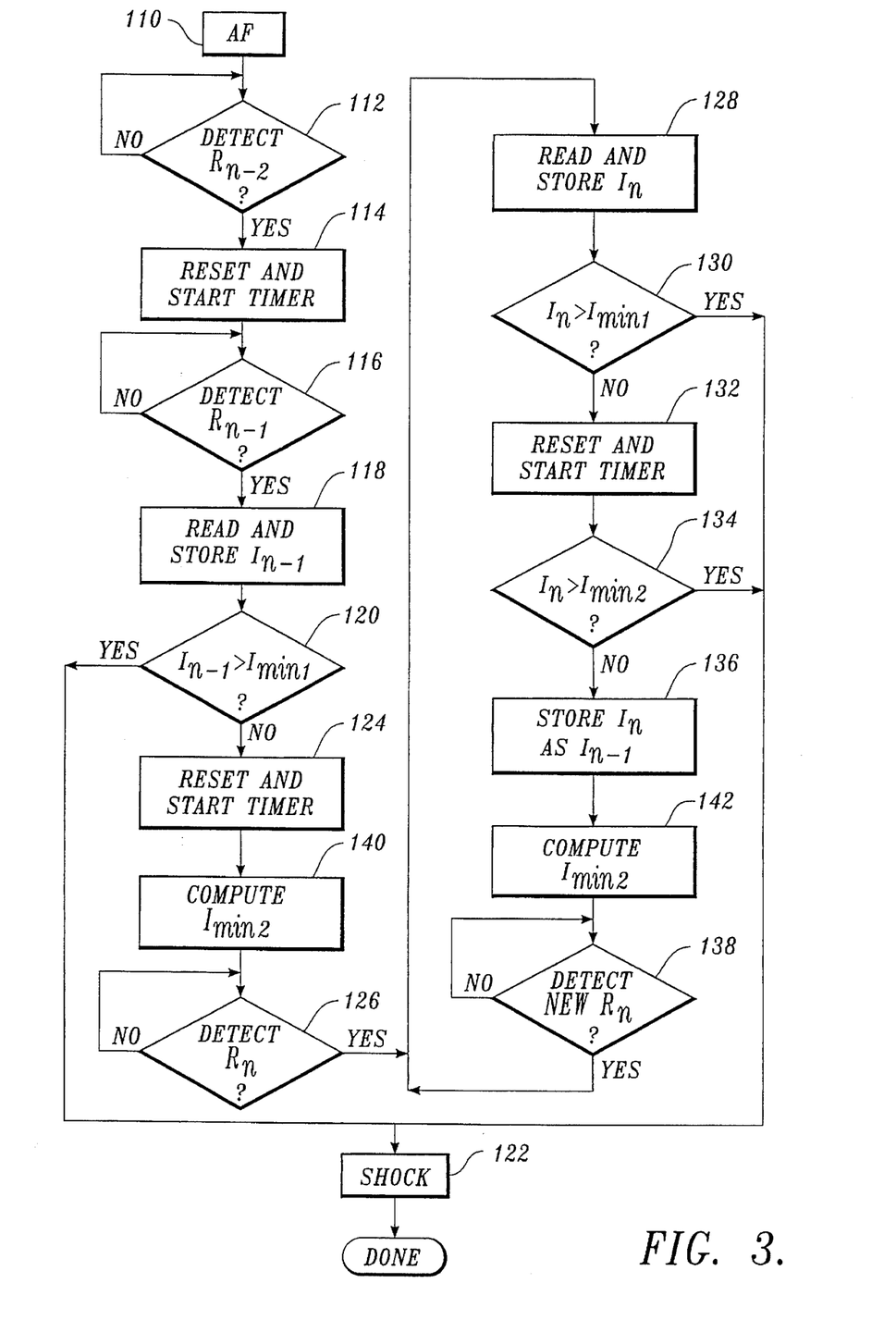
FIG. 3 is another flow diagram illustrating the manner in which the atrial defibrillator of FIG. 1 may be implemented in accordance with a second embodiment of the present invention.

Referring now to FIG. 3, it illustrates a further implementation embodying the present invention. The step sequence of the flow diagram of FIG. 3 is essentially identical to that of FIG. 2 and hence identical steps have been provided with identical reference numerals.

Here, all of the steps illustrated in FIG. 2 are performed in the same sequence, except additional steps 140 and 142 are interposed between steps 124 and 126 and 136 and 138, respectively. Steps 140 and 142 are provided for computation stage 80 to compute a second minimum time interval ($I_{min2}$) for comparison with the interval currently being timed and which is based upon the immediately preceding interval. Hence, in step 140, the second minimum time interval ($I_{min2}$) is computed based upon the first time interval ($I_{n-1}$) read and stored in step 118 and while the second time period is being timed.

Again, in steps 120 and 130, the first time interval ($I_{n-1}$) and the second time interval ($I_n$), respectively, are compared to a preselected minimum time interval ($I_{min1}$) such as, for example, eight hundred milliseconds (800 ms), considered safe regardless of the previous interval length. If the second time interval ($I_n$) as determined in step 130 is not longer than the preselected minimum time interval, timer 64 is first reset and started in step 132 and then step 134 is performed to determine if the second time interval ($I_n$) is longer than the second minimum time interval ($I_{min2}$) computed in step 140. During the performance of step 134, the second time interval may further be compared to the preselected fail safe minimum time interval as well, and as previously described.

If the outcome of step 134 is negative, it will be noted that step 136 is then performed wherein the second time interval is stored as the first time interval. A new second minimum time interval ($I_{min2}$) is computed in step 142 based upon the second time interval which, in step 136, was stored as a new first time interval. After a new third R wave ($R_n$) is detected in step 138, the new second time interval will be compared to the last computed second minimum time interval ($I_{min2}$) in step 134, if needed. Hence, for each interval currently being timed, a new second minimum time interval is computed based upon the immediately preceding interval.

The computed second minimum time interval may, for example, be equal to the preceding or first time interval ($I_{n-1}$) minus a third time interval. The third time interval may be a fixed interval of, for example, one hundred milliseconds (100 ms). As a result, to satisfy the criteria of step 132, the second time interval ($I_n$) must be greater than the first time interval ($I_{n-1}$) minus one hundred milliseconds (100 ms). This permits a wider range of R to R intervals to satisfy the energy delivery criteria while still assuring that energy is not delivered following a comparatively long-short interval sequence.

Alternatively, the computed second minimum time interval may be based upon the corrected QT interval of the patient. In doing so, the following relationship may be used to satisfy the criteria of step 132:

$$I_n > I_{min2} = K\sqrt{I_{n-1}} + C$$

where:

$I_n$ is the second time interval;

$I_{n-1}$ is the first time interval;

C is a constant; and $K = QT_c + 0.1\ QT_c$ where $QT_c$ is the corrected QT interval Determining the second minimum time interval in accordance with either of the above relationships will result in an atrial defibrillator which safely applies cardioverting electrical energy to the atria. This is achieved while increasing the probability of locating an R wave upon which to safely synchronize energy delivery.

While a particular embodiment of the present invention has been shown and described, modifications may be made, and it is therefore intended in the appended claims to cover all such changes and modifications which fall within the true spirit and scope of the invention.

What is claimed is:

1. An atrial defibrillator for providing cardioverting electrical energy to atria of a human heart, said atrial defibrillator comprising:

detecting means for detecting ventricular activations of the heart;

interval determining means for determining time intervals between immediately successive ventricular activations; and cardioverting means for applying the cardioverting electrical energy to the atria of the heart when a second time interval between a third ventricular activation and a second ventricular activation immediately preceding the third ventricular activation satisfies a predetermined criteria with respect to a first time interval between the second ventricular activation and a first ventricular activation immediately preceding said second ventricular activation.

2. An atrial defibrillator as defined in claim 1 wherein the cardioverting means includes means for determining if the second time interval is longer than the first time interval.

3. An atrial defibrillator as defined in claim 1 wherein the cardioverting means includes means for determining if the second time interval is longer than the first time interval minus a third time interval.

4. An atrial defibrillator as defined in claim 3 wherein said third time interval is a fixed time interval.

5. An atrial defibrillator as defined in claim 4 wherein said fixed time interval is about one hundred milliseconds.

6. An atrial defibrillator as defined in claim 1 wherein the cardioverting means applies the cardioverting electrical energy in timed relation to the third ventricular activation.

7. An atrial defibrillator as defined in claim 1 further including calculating means for calculating a minimum time interval based upon the first time interval and wherein the cardioverting means further includes means for determining if the second time interval is longer than the minimum time interval.

8. An atrial defibrillator as defined in claim 7 wherein the minimum time interval is proportional to the square root of the first time interval.

9. A cardiovertor for providing cardioverting electrical energy to a human heart, said cardiovertor comprising:

detecting means for detecting activations of the heart;

interval determining means for determining time intervals between immediately successive activations; and cardioverting means for applying the cardioverting electrical energy to the heart when a second time interval between a third activation and a second activation immediately preceding the third activation satisfies a predetermined criteria with respect to a first time interval between the second activation and a first activation immediately preceding said second activation.

10. A method of providing cardioverting electrical energy to atria of a human heart, said method including the steps of:

detecting ventricular activations of the heart;

determining time intervals between immediately successive ventricular activations; and applying the cardioverting electrical energy to the atria of the heart when a second time interval between a third ventricular activation and a second ventricular activation immediately preceding the third ventricular activation satisfies a predetermined criteria with respect to a first time interval between the second ventricular activation and a first ventricular activation immediately preceding said second ventricular activation.

11. A method as defined in claim 10 including the further step of determining when the second time interval is longer than the first time interval to satisfy the predetermined criteria.

12. A method as defined in claim 10 including the further step of determining when the second time interval is longer than the first time interval minus a third time interval to satisfy the predetermined criteria.

13. A method as defined in claim 10 including the further step of determining when the second time interval is longer than the first time interval minus a constant to satisfy the predetermined criteria.

14. A method as defined in claim 10 wherein the applying step includes applying the cardioverting electrical energy in timed relation to the third ventricular activation.

15. A method as defined in claim 10 including the further step of calculating a minimum time interval based upon the first time interval and wherein the predetermined criteria is the second time interval being longer than the minimum time interval.

16. A method as defined in claim 10 including the further step of calculating the minimum time interval based upon is proportional the square root of the first time interval and wherein the predetermined criteria is the second time interval being longer than the minimum time interval.

17. A method for providing cardioverting electrical energy to a human heart, said method including the steps of:

detecting activations of the heart;

determining time intervals between immediately successive activations; and applying the cardioverting electrical energy to the heart when a second time interval between a third activation and a second activation immediately preceding the third activation satisfies a predetermined criteria with respect to a first time interval between the second activation and an activation immediately preceding said second activation.

* * * * *

UNITED STATES PATENT AND TRADEMARK OFFICE
CERTIFICATE OF CORRECTION

PATENT NO. : 5,486,198
DATED : January 23, 1996
INVENTOR(S) : Gregory M. Ayers, et al It is certified that error appears in the above-identified patent and that said Letters Patent is hereby corrected as shown below:

| Column | Line | |
|--------|------|---|
| 10 | 61 | after --upon-- delete "is" |
| 10 | 62 | before--the-- delete "proportional" |

Signed and Sealed this

Eighteenth Day of June, 1996

Attest:

BRUCE LEHMAN

Attesting Officer

Commissioner of Patents and Trademarks